(12) United States Patent
Uchiyama et al.

(10) Patent No.: US 6,468,515 B1
(45) Date of Patent: Oct. 22, 2002

(54) HAIR CONDITIONING COMPOSITION COMPRISING HIGH MOLECULAR WEIGHT ESTER OIL

(75) Inventors: Hirotaka Uchiyama; Yukiko Mizoguchi, both of Kobe; Arata Mitsumatsu, Hyogo, all of (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/508,860

(22) PCT Filed: Jun. 4, 1998

(86) PCT No.: PCT/US98/11781

§ 371 (c)(1),
(2), (4) Date: Jun. 19, 2000

(87) PCT Pub. No.: WO99/13838

PCT Pub. Date: Mar. 25, 1999

(51) Int. Cl.[7] .......................... A61K 7/06; A61K 7/075; A61K 7/08
(52) U.S. Cl. ................ 424/70.27; 424/70.1; 424/70.11; 424/70.12; 424/70.28
(58) Field of Search ............................ 424/70.1, 70.11, 424/70.12, 70.27, 70.28

(56) References Cited

FOREIGN PATENT DOCUMENTS

| DE | 4337169 A1 | 5/1995 | ............ A61K/7/06 |
|---|---|---|---|
| EP | 0517371 A2 | 12/1992 | ............ A61K/7/06 |
| WO | WO 98/24402 | 6/1998 | ........... A61K/7/075 |

*Primary Examiner*—Thurman K. Page
*Assistant Examiner*—Humera N. Sheikh
(74) *Attorney, Agent, or Firm*—Linda M. Sivik; Andrew A. Paul; Tara M. Rosnell

(57) ABSTRACT

Disclosed is a hair conditioning composition comprising. (1) a high molecular weight ester oil being water-insoluble, having a molecular weight of at least about 800, and in liquid form at 25° C., the high molecular weight ester oil selected from the group consisting of: a) pentaerythritol ester oils, b) trimethylol ester oils, and mixtures thereof; (2) a hydrophilically substituted cationic surfactant; (3) a high melting point compound having a melting point of at least 25° C.; and (4) an aqueous carrier.

9 Claims, No Drawings

HAIR CONDITIONING COMPOSITION COMPRISING HIGH MOLECULAR WEIGHT ESTER OIL

This application is a 371 of PCT/US98/11781 filed Jun. 4, 1998.

TECHNICAL FIELD

The present invention relates to hair conditioning compositions comprising a high molecular weight ester oil. More specifically, the present invention relates to hair conditioning compositions comprising a high molecular weight ester oil, a hydrophilically substituted cationic surfactant, and a high melting point compound.

BACKGROUND

Human hair becomes soiled due to its contact with the surrounding environment and from sebum secreted by the scalp. The soiling of the hair causes it to have a dirty or greasy feel, and an unattractive appearance. The soiling of the hair necessitates shampooing with regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of stabc upon drying which can interfere with combing and result in a condition commonly referred to as "fly-away hair", or contribute to an undesirable phenomena of "split ends", particularly for long hair.

A variety of approaches have been developed to alleviate these after-shampoo problems. These approaches range from post-shampoo application of hair conditioner such as leave-on and rinse-off products, to hair conditioning shampoos which attempt to both cleanse and condition the hair from a single product. Although some consumers prefer the ease and convenience of a shampoo which includes conditioners, a substantial proportion of consumers prefer the more conventional conditioner formulations which are applied to the hair as a separate step from shampooing, usually subsequent to shampooing. Conditioning formulations can be in the form of rinse-off products or leave-on products, and can be in the form of an emulsion, cream, gel, spray, and mousse. Such consumers who prefer the conventional conditioner formulations value the relatively higher conditioning effect, or convenience of changing the amount of conditioning depending on the condition of hair or portion of hair.

A common method of providing conditioning benefit to the hair is through the use of hair conditioning agents such cationic surfactants and polymers, silicone conditioning agents, hydrocarbon oils, and fatty alcohols.

Cationic surfactants and polymers, hydrocarbon oils and fatty alcohols are known to enhance hair shine and provide moistness, softness, and static control to the hair. However, such components can also provide stickiness or greasy or waxy feeling, particularly when the hair is dried. Silicone conditioning agents are also known to provide conditioning benefits such as smoothness and combing ease due to the low surface tension of silicone compounds. However, silicone conditioning agents can cause dry feel or frizzy condition to the hair, again, particularly when the hair is dried.

Based on the foregoing, there remains a desire to provide hair conditioning compositions which provide improved conditioning benefits both when the hair is wet and when the hair is dried. Specifically, there is a need to provide long lasting moisturized feel, smooth feel, and manageability control to the hair when the hair is dried, yet not leave the hair feeling greasy.

None of the existing art provides all of the advantages and benefits of the present invention.

SUMMARY

The present invention is directed to a hair conditioning composition comprising:

(1) a high molecular weight ester oil being water-insoluble, having a molecular weight of at least about 800, and in liquid form at 25° C., the high molecular weight ester oil selected from the group consisting of:

a) pentaerythritol ester oils of the following formula:

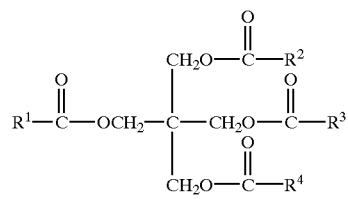

wherein $R^1$, $R^2$, $R^3$, and $R^4$, independently, are branched, straight, saturated, or unsaturated alkyl, aryl, and alkylaryl groups having from 1 to about 30 carbons;

b) trimethylol ester oils of the following formula:

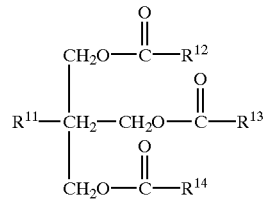

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons; and mixtures thereof;

(2) a hydrophilically substituted cationic surfactant;

(3) a high melting point compound having a melting point of at least 25° C.; and (4) an aqueous carrier.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

All cited references are incorporated herein by reference in their entireties. Citation of any reference is not an admission regarding any determination as to its availability as prior art to the claimed invention.

Herein, "comprising" means that other steps and other ingredients which do not affect the end result can be added.

This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

The aspects and embodiments of the present invention set forth in this document have many advantages. For example, the hair conditioning compositions of the present invention provide long lasting moisturized feel, smooth feel, and manageability control to the hair when the hair is dried, yet not leave the hair feeling greasy. The hair conditioning compositions of the present invention are suitable for product forms to leave on the hair, or rinse off from the hair.

HIGH MOLECULAR WEIGHT ESTER OIL

The hair conditioning composition of the present invention comprises a high molecular weight ester oil selected from the group consisting of pentaerythritol ester oils, trimethylol ester oils, and mixtures thereof. The high molecular weight ester oils useful herein are those which are water-insoluble, have a molecular weight of at least about 800, and are in liquid form at 25° C. As used herein, the term "water-insoluble" means the compound is substantially not soluble in water at 25° C.; when the compound is mixed with water at a concentration by weight of above 1.0%, preferably at above 0.5%, the compound is temporarily dispersed to form an unstable colloid in water, then is quickly separated from water into two phases.

The high molecular weight ester oil herein provides conditioning benefits such as moisturized feel, smooth feel, and manageability control to the hair when the hair is dried, yet not leave the hair feeling greasy. It is believed that water-insoluble oily material in general are capable of being deposited on the hair. Without being bound by theory, it is believed that, because of its bulkiness, the high molecular weight ester oil covers the surface of the hair and, as a result, the high molecular weight ester oil reduces hair friction to deliver smoothness and manageability control to the hair. It is also believed that, because it has some hydrophilic groups, the high molecular weight ester oil provides moisturized feel, yet, because it is liquid, does not leave the hair feeling greasy. The high molecular weight ester oil is chemically stable under normal use and storage conditions.

The high molecular weight ester oil is preferably included in the composition at a level by weight of from about 0.1% to about 20%, preferably from about 0.2% to about 10%, more preferably from about 0.5% to about 5%.

Pentaerythritol ester oils useful herein are those having the following formula:

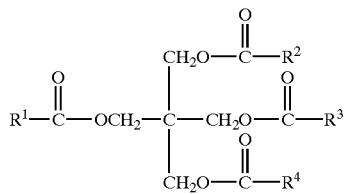

wherein $R^1$, $R^2$, $R^3$, and $R^4$, independently, are branched, straight, saturated, or Oo unsaturated alkyl, aryl, and alkylaryl groups having from 1 to about 30 carbons. Preferably, $R^1$, $R^2$, $R^3$, and $R^4$, independently, are branched, straight, saturated, or unsaturated alkyl groups having from about 8 to about 22 carbons. More preferably, $R^1$, $R^2$, $R^3$ and $R^4$ are defined so that the molecular weight of the compound is from about 800 to about 1200.

Trimethylol ester oils useful herein are those having the following formula:

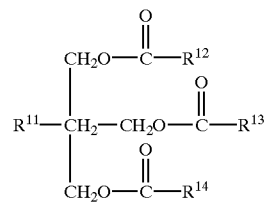

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons. Preferably, $R^1$ is ethyl and $R^{12}$, $R^{13}$, and $R^{14}$, independently, are branched, straight, saturated, or unsaturated alkyl groups having from 8 to about 22 carbons. More preferably, $R^{11}$, $R^{12}$, $R^{13}$ and $R^{14}$ are defined so that the molecular weight of the compound is from about 800 to about 1200.

Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

HYDROPHILICALLY SUBSTITUTED CATIONIC SURFACTANT

The hair conditioning composition of the present invention comprises a hydrophilically substituted cationic surfactant. The hydrophilically substituted cationic surfactant herein include those which include at least 2 hydrophilic moieties wherein at least 1 substituent in the molecule selected from aromatic ether ester, amido or amino moieties, and at least 1 substituent selected from alkoxy (preferably $C_1$–$C_3$ alkyoxy), polyoxyalkylene (preferably $C_1$–$C_3$ polyoxyalkylene), alkyl amido, hydroxyalkyl, and alkyl ester groups. Preferably, the hydrophilically substituted cationic surfactants herein contain from 2 to about 10 nonionic hydrophilic moieties.

The hydrophilically substituted cationic surfactant herein provides conditioning benefits such as smooth feel to the hair, particularly when the hair is dried. It is believed that, by combining the hydrophilically substituted cationic surfactant with the high molecular weight ester oil mentioned above, a conditioning composition which provides improved conditioning benefit both when the hair is wet and dried can be provided.

The hydrophilically substituted cationic surfactant is preferably included in the composition at a level by weight of from about 0.1% to about 20%, preferably from about 0.2% to about 10%, more preferably from about 0.5% to about 5%.

Suitable hydrophilically substituted cationic surfactants include those of the formula (II) through (Vlll) below:

(II)

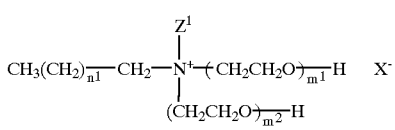

wherein $n^1$ is from 8 to about 28, $m^1+m^2$ is from 2 to about 40, $Z^1$ is a short chain alkyl, preferably a $C_1$–$C_3$ alkyl, more preferably methyl, or $(CH_2CH_2O)_{m3}H$ wherein $m^1+m^2+m^3$ is up to 60, and X is a salt forming anion such as those selected from halogen, (e.g. chloride, bromide), acetate, citrate, lactate, glycolate, phosphate, nitrate, sulfonate, sulfate, alkylsulfate, and alkyl sulfonate radicals;

(III)

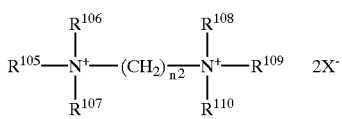

wherein $n^2$ is 1 to 5, one or more of $R^{105}$, $R^{106}$, and $R^{107}$ are independently an $C_1$–$C_{30}$ alkyl, the remainder are $CH_2CH_2OH$, one or two of $R^{108}$, $R^{109}$, and $R^{110}$ are independently an $C_1$–$C_{30}$ alkyl, and remainder are $CH_2CH_2OH$, and X is a salt forming anion as mentioned above;

(IV)

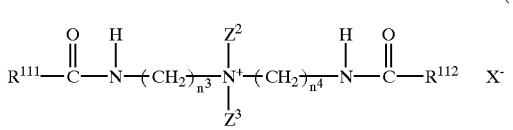

(V)

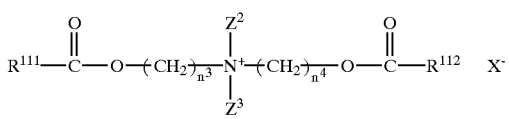

wherein, independently for formulae (IV) and (V), $Z^2$ is an alkyl, preferably $C_1$–$C_3$ alkyl, more preferably methyl, and $Z^3$ is a short chain hydroxyalkyl, preferably hydroxymethyl or hydroxyethyl, $n^3$ and $n^4$ independently are integers from 2 to 4, inclusive, preferably from 2 to 3, inclusive, more preferably 2, $R^{111}$ and $R^{112}$, independently, are substituted or unsubstituted hydrocarbyls, $C_{12}$–$C_{20}$ alkyl or alkenyl, and X is a salt forming anion as defined above;

(VI)

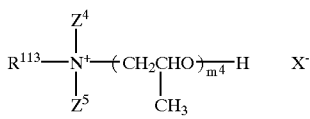

wherein $R^{113}$ is a hydrocarbyl, preferably a $C_1$–$C_3$ alkyl, more preferably methyl, $Z^4$ and $Z^5$ are, independently, short chain hydrocarbyls, preferably $C_2$–$C_4$ alkyl or alkenyl, more preferably ethyl, $m^4$ is from 2 to about 40, preferably from about 7 to about 30, and X is a salt forming anion as defined above;

(VII)

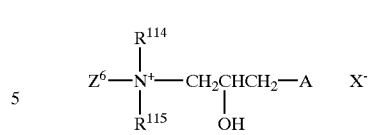

wherein $R^{114}$ and $R^{115}$, independently, are $C_1$–$C_3$ alkyl, preferably methyl, $Z^6$ is a $C_{12}$–$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

(VIII)

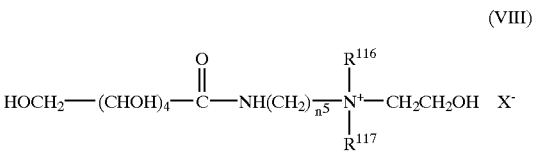

wherein $n^5$ is 2 or 3, $R^{116}$ and $R^{117}$, independently are $C_1$–$C_3$ hydrocarbyls preferably methyl, and X is a salt forming anion as defined above.

Nonlimiting examples of hydrophilically substituted cationic surfactants useful in the present invention include the materials having the following CTFA designations: quaternium-16, quaternium-26, quaternium-27, quaternium-30, quaternium-33, quaternium43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium- 78, quaternium- 79 hydrolyzed collagen, quatemium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quatemium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemical, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD 0112PG, ETHOQUAD C/25, ETHOQUAD S/25, and ETHODUOQUAD from Akzo, DEHYQUAT SP from Henkel, and ATLAS G265 from ICI Americas.

HIGH MELTING POINT COMPOUND

The hair conditioning composition of the present invention comprises a high melting point compound having a melting point of at least about 25° C. selected from the group consisting of fatty alcohols, fatty acids, fatty alcohol derivatives, fatty acid derivatives, hydrocarbons, steroids, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

It is believed that these high melting point compounds cover the hair surface and reduce friction, thereby resulting in providing smooth feel on the hair and ease of combing.

The high melting point compound is preferably included in the composition at a level by weight of from about 1% to about 14%, preferably from about 3% to about 10%, more preferably from about 4% to about 8%.

The fatty alcohols useful herein are those having from about 14 to about 30 carbon atoms, preferably from about 16 to about 22 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$–$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneg lycol monostea rate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

Hydrocarbons useful herein include compounds having at least about 20 carbons.

Steroids useful herein include compounds such as cholesterol.

High melting point compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Commercially available high melting point compounds useful herein include: cetyl alcohol, stearyl alcohol, and behenyl alcohol having tradenames KONOL series available from Shin Nihon Rika (Osaka, Japan), and NMAseries available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from witco Corp. (Dublin Ohio, USA), and DERMA available from Vevy (Genova, Italy); and cholesterol having tradename NIKKOL AGUASOME LA available from Nikko.

AQUEOUS CARRIER

The compositions of the present invention comprise an aqueous carrier. The level and species of the carrier are selected according to the compatibility with other components, and other desired characteristic of the product.

Carriers useful in the present invention include water and water solutions of lower alkyl alcohols and polyhydric alcohols. Lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 95%, preferably from about 30% to about 92%, and more preferably from about 50% to about 90% water.

TERTIARY AMIDO AMINE AND ACID

The hair conditioning composition of the present invention may further comprise a tertiary amido amine having an alkyl group of from about 12 to about 22 carbons.

The tertiary amido amine herein also provides conditioning benefits such as smooth feel to the hair, particularly when the hair is dried. It is further believed that, by combining the tertiary amido amine with the hydrophilically substituted cationic surfactant and the high molecular weight ester oil mentioned above, a conditioning composition having a layered gel structure can be obtained.

A layered gel structure can be distinguished from spherical crystalline phase structures. By definition, spherical crystalline phase structures include, for example, phases encompassing solid crystals at randomly, the M-phase structure as defined in pages 83 to 84 of "Physicochemistry of Cetyl Alcohol" issued by Fragrance Journal Ltd. 1992, and onion-like spherical layers of liquid crystals as taught in Japanese Kokai Patent Publication (A) S61-286311. Without being bound by theory, it is believed that the solid crystals andlor liquid crystals of high melting point compounds contained in spherical crystalline phase structures cannot be effectively spread onto and deposited on the surface of the hair. Consequently, the high melting point compounds incorporated in spherical crystalline phase structures contribute less than those included incorporated in a layered gel structure with regard to providing conditioning benefit to the hair.

The tertiary amido amine is preferably included in the composition at a level by weight of from about 0.1% to about 20%, preferably from about 0.2% to about 10%, more preferably from about 1% to about 5%.

Particularly useful tertiary amido amines herein include: stearamidopropyldimethylamine, stearamidopropyldiethylamine, stearamidoethyldiethylamine, stearamidoethyldimethylamine, palmitamidopropyidimethylamine, palmitamidopropyldiethylamine, palmitamidoethyidiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. Also useful herein are those tertiary amido amines disclosed in U.S. Pat. No. 4,275,055, Nachtigal, et al.

These tertiary amido amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid.

The tertiary amido amine herein is preferably partially neutralized with any of these acids at a molar ratio of the tertiary amido amine to the acid of from about 1:0.3 to about 1:2, more preferably from about 1:0.4 to about 1:1.

SILICONE COMPOUND

The hair conditioning composition of the present invention may further comprise a silicone compound. The silicone compounds useful herein include volatile soluble or insoluble, or nonvolatile soluble or insoluble silicone conditioning agents. By soluble what is meant is that the silicone compound is miscible with the carrier of the composition so as to form part of the same phase. By insoluble what is meant is that the silicone forms a separate, discontinuous phase from the carrier, such as in the form of an emulsion or a suspension of droplets of the silicone. The silicone compounds herein may be made by any suitable method known in the art, including emulsion polymerization. The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

The silicone compounds for use herein will preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970. Silicone compound of high molecular weight may be made by emulsion polymerization. Suitable silicone fluids include polyalkyl siloxanes, polyaryl siloxanes, polyalkylaryl siloxanes, polyether siloxane copolymers, and mixtures thereof. Other nonvolatile silicone compounds having hair conditioning properties can also be used.

The silicone compound is preferably included in the composition at a level by weight from about 0.01% to about 20%, more preferably from about 0.05% to about 10%.

The silicone compounds herein also include polyalkyl or polyaryl siloxanes with the following structure (I)

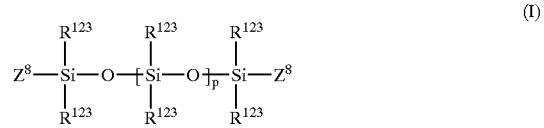

wherein $R^{123}$ is alkyl or aryl, and x is an integer from about 7 to about 8,000. $Z^8$ represents groups which block the ends of the silicone chains. The alkyl or aryl groups substituted on the siloxane chain ($R^{123}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{123}$ groups on the silicon atom may represent the same group or different groups. Preferably, the two $R^{123}$ groups represent the same group. Suitable $R^{123}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

The silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other silicone compounds include amino substituted materials. Suitable alkylamino substituted silicone compounds include those represented by the following structure (II)

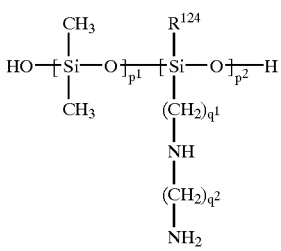

(II)

wherein $R^{124}$ is H, $CH_3$ or OH, $p^1$, $p^2$, $q^1$ and $q^2$ are integers which depend on the molecular weight, the average molecular weight being approximately between 5,000 and 10,000. This polymer is also known as "amodimethicone".

Suitable amino substituted silicone fluids include those represented by the formula (III)

$$(R^{125})_a G_{3-a} \text{—Si—}(OSiG_2)_{p3}\text{—}(OSiG_b(R^{125})_{2-b})_{p4}\text{—O—}SiG_{3-a}(R^{125})_a \quad (III)$$

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum $p^3+p^4$ is a number from 1 to 2,000 and preferably from 50 to 150, $p^3$ being able to denote a number from 0 to 1,999 and preferably from 49 to 149 and $p^4$ being able to denote an integer from 1 to 2,000 and preferably from 1 to 10; $R^{125}$ is a monovalent radical of formula $C_{q3}H_{2q3}L$ in which $q^3$ is an integer from 2 to 8 and L is chosen from the groups

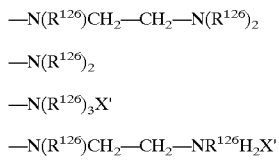

in which $R^{126}$ is chosen from the group consisting of hydrogen, phenyl, benzyl, a saturated hydrocarbon radical, preferably an alkyl radical containing from 1 to 20 carbon atoms, and X' denotes a halide ion.

An especially preferred amino substituted silicone corresponding to formula (III) is the polymer known as "trimethylsilylamodimethicone" wherein $R^{124}$ is $CH_3$.

Other amino substituted silicone polymers which can be used are represented by the formula (V):

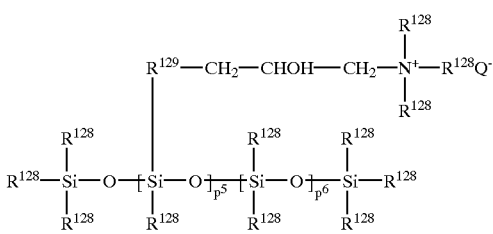

(V)

where $R^{128}$ denotes a monovalent hydrocarbon radical having from 1 to 18 carbon atoms, preferably an alkyl or alkenyl radical such as methyl; $R^{129}$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; $p^5$ denotes an average statistical value from 2 to 20, preferably from 2 to 8; $p^6$ denotes an average statistical value from 20 to 200, and preferably from 20 to 50. A preferred polymer of this class is available from Union Carbide under the name "UCAR SILICONE ALE 56."

References disclosing suitable nonvolatile dispersed silicone compounds include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston. "Silicon Compounds" distributed by Petrarch Systems, Inc., 1984, provides an extensive, though not exclusive, listing of suitable silicone compounds.

Another nonvolatile dispersed silicone that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the abovedisclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, poly (dimethylsiloxane methylvinylsiloxane) copolymer, poly (dimethylsiloxane diphenylsiloxane methylvinylsiloxane) copolymer and mixtures thereof.

Also useful are silicone resins, which are highly crosslinked polymeric siloxane systems. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsesquioxane, which is commercially available as Tospearl™ from Toshiba Silicones.

The method of manufacturing these silicone compounds, can be found in Encyclopedia of Polymer Science and Engineering, Volume 15, Second Edition, pp. 204–308, John Wiley & Sons, Inc., 1989.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO1.5$; and Q denotes the quadri- or tetra-functional unit SiO2. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

Commercially available silicone compounds which are useful herein include Dimethicone with tradename D-130, cetyl Dimethicone with tradename DC2502, stearyl Dimethicone with tradename DC2503, emulsified polydimethyl siloxanes with tradenames DC1664 and DC1784, and alkyl grafted copolymer silicone emulsion with tradename DC2-2845; all available from Dow Corning Corporation, and emulsion polymerized Dimethiconol available from Toshiba Silicone as described in GB application 2,303,857.

ADDITIONAL COMPONENTS

The hair conditioning compositions of the present invention may contain a variety of additional components, which may be selected by the artisan according to the desired characteristics of the final product. Additional components include, for example, hydrophobic cationic surfactants, cationic polymers, additional oily compounds, nonionic polymers, and other additional components.

Hydrophobic Cationic Surfactant

The hydrophobic cationic surfactants useful herein are any known to the artisan.

Among the hydrophobic cationic surfactants useful herein are those corresponding to the general formula (I):

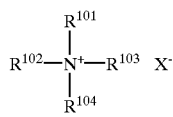

(I)

wherein at least one of $R^{101}$, $R^{102}$, $R^{103}$ and $R^{104}$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^{101}$, $R^{102}$, $R^{103}$ and $R^{104}$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^{101}$, $R^{102}$, $R^{103}$ and $R^{104}$ are independently selected from $C_1$ to about $C_{22}$ alkyl. Nonlimiting examples of hydrophobic cationic surfactants useful in the present invention include the materials having the following CTFA designations: quatemium-8, quaternium-14, quaternium-18, quatemium-18 methosulfate, quaternium-24, and mixtures thereof.

Among the hydrophobic cationic surfactants of general formula (I), preferred are those containing in the molecule at least one alkyl chain having at least 16 carbons. Nonlimiting examples of such preferred hydrophobic cationic surfactants include: behenyl trimethyl ammonium chloride available, for example, with tradename INCROQUAT TMC-80 from Croda and ECONOL TM22 from Sanyo Kasei; cetyl trimethyl ammonium chloride available, for example, with tradename CA-2350 from Nikko Chemicals, hydrogenated tallow alkyl trimethyl ammonium chloride, dialkyl (14–18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Cationic Polymers

The hair conditioning compositions of the present invention may contain one or more cationic polymers. As used herein, the term "polymer" shall include materials whether made by polymerization of one type of monomer or made by two (i.e., copolymers) or more types of monomers.

Preferably, the cationic polymer is a water-soluble cationic polymer. By "water soluble" cationic polymer, what is meant is a polymer which is sufficiently soluble in water to form a substantially clear solution to the naked eye at a concentration of 0.1% in water (distilled or equivalent) at 25° C. The preferred polymer will be sufficiently soluble to form a substantially clear solution at 0.5% concentration, more preferably at 1.0% concentration.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density is preferably at least about 0.1 meq/gram, more preferably at least about 1.5 meq/gram, even more preferably at least about 1.1 meq/gram, still more preferably at least about 1.2 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalitbes with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred. Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quatemized by reaction with a salt of the formula $R^{118}X$ wherein $R^{118}$ is a short chain alkyl, preferably a $C_1$–$C_7$ alkyl, more preferably a $C_1$–$C_3$ alkyl, and X is a salt forming anion as defined above.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, NJ, USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyidiallylammonium chloride homopolymer and copolymers of acrylamide and dimethyldiallylammonium chloride, referred to in the industry (CTFA) as Polyquatemium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256.

Other suitable cationic polymers are amphoteric terpolymers consisting of acrylic acid methacrylamidopropyl trimethylammonium chloride and methyl acrylate, having a structure as shown below referred to in the industry (CTFA) as Polyquaternium 47. An example of a suitable commerical material is MERQUAT 2001® wherein the ratio of $n^6$:$n^7$:$n^8$ is 45:45:10 supplied by Calgon Corp.

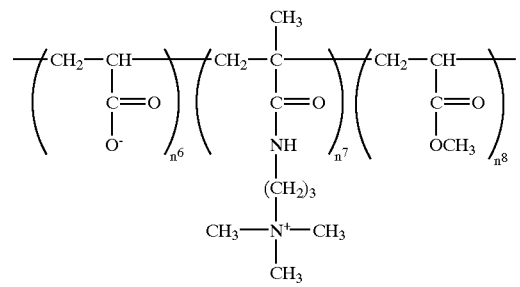

Other cationic polymers that can be used include polysaccharide polymers, such as cationic cellulose derivatives and cationic starch derivatives.

Cationic polysaccharide polymer materials suitable for use herein include those of the formula:

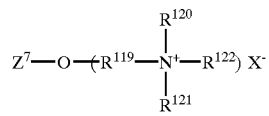

wherein: $Z^7$ is an anhydroglucose residual group, such as a starch or cellulose anhydroglucose residual, $R^{119}$ is an alkylene oxyalkylene, polyoxyalkylene, or 10 hydroxyalkylene group, or combination thereof, $R^{120}$, $R^{121}$, and $R^{122}$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^{120}$, $R^{121}$ and $R^{122}$) preferably being about 20 or less, and X is as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are, available from Amerchol Corp. (Edison, N.J., USA) under the tradename Polymer LM-200®.

Other cationic polymers that can be used include cationic guar gum derivatives, such as guar hydroxypropyltrimonium chloride commercially available from Celanese Corp. in their Jaguar R series. Other materials include quaternary nitrogen-containing cellulose ethers as described in U.S. Pat. No. 3,962,418, and copolymers of etherified cellulose and starch as described in U.S. Pat. No. 3,958,581.

Particularly useful cationic polymers herein include Polyquaternium-7, Polyquaternium-10, Polyquaternium-24, Polyquaternium-39, Polyquaternium-47, and mixtures thereof.

Additional Oily Compounds

Additional oily compounds useful herein include fatty alcohols and their derivatives, fatty acids and their derivatives, and hydrocarbons. The additional oily compounds useful herein may be volatile or nonvolatile, and have a melting point of not more than about 25° C. Without being bound by theory, it is believed that, the additional oily compounds may penetrate into the hair to modify the hydroxy bonds of the hair, thereby resulting in providing softness and flexibility to the hair. The additional oily compounds of this section are to be distinguished from the high melting point compounds described above. Nonlimiting examples of the additional oily compounds are found in International Cosmetic Ingredient Dictionary, Fifth Edition, 1993, and CTFA Cosmetic Ingredient Handbook, Second Edition, 1992.

The fatty alcohols useful herein include those having from about 10 to about 30 carbon atoms, preferably from about 12 to about 22 carbon atoms, and more preferably from about 16 to about 22 carbon atoms. These fatty alcohols can be straight or branched chain alcohols and can be saturated or unsaturated alcohols, preferably unsaturated alcohols. Nonlimiting examples of these compounds include oleyl alcohol, palmitoleic alcohol, isostearyl alcohol, isocetyl alchol, undecanol, octyl dodecanol, octyl decanol, octyl alcohol, caprylic alcohol, decyl alcohol and lauryl alcohol.

The fatty acids useful herein include those having from about 10 to about carbon atoms, preferably from about 12 to about 22 carbon atoms, and more preferably from about 16 to about 22 carbon atoms. These fatty acids can be straight or branched chain acids and can be saturated or unsaturated. Suitable fatty acids include, for example, oleic acid, linoleic acid, isostearic acid, linolenic acid, ethyl linolenic acid, ethyl linolenic acid, arachidonic acid, and ricinolic acid.

The fatty acid derivatives and fatty alcohol derivatives are defined herein to include, for example, esters of fatty alcohols, alkoxylated fatty alcohols, alkyl ethers of fatty alcohols, alkyl ethers of alkoxylated fatty alcohols, and bulky ester oils such as pentaerythritol ester oils, trimethylol ester oils, citrate ester oils, glyceryl ester oils, and mixtures thereof. Nonlimiting examples of fatty acid derivatives and fatty alcohol derivatives, include, for example, methyl linoleate, ethyl linoleate, isopropyl linoleate, isodecyl oleate, isopropyl oleate, ethyl oleate, octyidodecyl oleate, oleyl oleate, decyl oleate, butyl oleate, methyl oleate, octyidodecyl stearate, octyldodecyl isostearate, octyldodecyl isopalmitate, octyl isopelargonate, octyl pelargonate, hexyl isostearate, isopropyl isostearate, isodecyl isononanoate, isopropyl isostearate, ethyl isostearate, methyl isostearate and Oleth-2. Bulky ester oils such as pentaerythritol ester oils, trimethylol ester oils, citrate ester oils and glyceryl ester oils useful herein are those which have a molecular weight of less than about 800, preferably less than about 500.

The hydrocarbons useful herein include straight chain, cyclic, and branched chain hydrocarbons which can be either saturated or unsaturated, so long as they have a melting point of not more than about 25° C. These hydrocarbons have from about 12 to about 40 carbon atoms, preferably from about 12 to about 30 carbon atoms, and preferably from about 12 to about 22 carbon atoms. Also encompassed herein are polymeric hydrocarbons of alkenyl monomers, such as polymers of $C_{2-6}$ alkenyl monomers. These polymers can be straight or branched chain polymers. The straight chain polymers will typically be relatively short in length, having a total number of carbon atoms as described above. The branched chain polymers can have substantially higher chain lengths. The number average molecular weight of such materials can vary widely, but will typically be up to about 500, preferably from about 200 to about 400, and more preferably from about 300 to about 350. Also useful herein are the various grades of mineral oils. Mineral oils are liquid mixtures of hydrocarbons that are obtained from petroleum. Specific examples of suitable hydrocarbon materials include paraffin oil, mineral oil, dodecane, isododecane, hexadecane, isohexadecane, eicosene, isoeicosene, tridecane, tetradecane, polybutene, polyisobutene, and mixtures thereof. Preferred for use herein are hydrocarbons selected from the group consisting of mineral oil, poly a-olefin oils such as isododecane, isohexadecane, polybutene, polyisobutene, and mixtures thereof.

Commercially available fatty alcohols and their derivatives useful herein include: oleyl alcohol with tradename UNJECOL 90BHR available from Shin Nihon Rika, various liquid esters with tradenames SCHERCEMOL series available from Scher, and hexyl isostearate with a tradename HIS and isopropryl isostearate having a tradename ZPIS available from Kokyu Alcohol. Commercially available bulky ester oils useful herein include: trimethylolpropane tricaprylateltricaprate with tradename MOBIL ESTER P43 from Mobil Chemical Co. Commercially available hydrocarbons useful herein include isododecane, isohexadeance, and isoeicosene with tradenames PERMETHYL 99A, PERMETHYL 101A, and PERMETHYL 1082, available from Presperse (South Plainfield N.J., USA), a copolymer of isobutene and normal butene with tradenames INDOPOL H-100 available from Amoco Chemicals (Chicago Ill., USA), mineral oil with tradename BENOL available from Witco, isoparaffin with tradename ISOPAR from Exxon Chemical Co. (Houston Tex., USA), and polydecene with tradename PURESYN 6 from Mobil Chemical Co.

Nonionic Polymers

Nonionic polymers useful herein include cellulose derivatives, hydrophobically modified cellulose derivatives, ethylene oxide polymers, and ethylene oxide/propylene oxide based polymers. Suitable nonionic polymers are cellulose derivatives including methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Herculus. Other suitable nonionic polymers are ethylene oxide and/or propylene oxide based polymers with tradenames CARBOWAX PEGs, POLYOX WASRs, and UCON FLUIDS, all supplied by Amerchol.

Polyethylene Glycols

The polyalkylene glycols are characterized by the general formula:

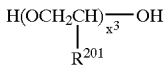

wherein $R^{201}$ is selected from the group consisting of H, methyl, and mixtures thereof. When $R^{201}$ is H, these materials are polymers of ethylene oxide, which are also known as polyethylene oxides, polyoxyethylenes, and polyethylene glycols. When $R^{201}$ is methyl, these materials are polymers of propylene oxide, which are also known as polypropylene oxides, polyoxypropylenes, and polypropylene glycols. When $R^{201}$ is methyl, it is also understood that various positional isomers of the resulting polymers can exist.

In the above structure, x3 has an average value of from about 1500 to about 25,000, preferably from about 2500 to about 20,000, and more preferably from about 3500 to about 15,000.

Other useful polymers include the polypropylene glycols and mixed polyethylenelpolypropylene glycols.

Polyethylene glycol polymers useful herein are PEG-2M wherein $R^{201}$ equals H and x3 has an average value of about 2,000 (PEG-2M is also known as Polyox WSR® N-10, which is available from Union Carbide and as PEG-2,000); PEG-5M wherein $R^{201}$ equals H and x3 has an average value of about 5,000 (PEG-5M is also known as Polyox WSR® N-35 and Polyox WSR® N-80, both available from Union Carbide and as PEG-5,000 and Polyethylene Glycol 300, 000); PEG-7M wherein $R^{201}$ equals H and x3 has an average value of about 7,000 (PEG-7M is also known as Polyox WSR® N-750 available from Union Carbide); PEG-9M wherein $R^{201}$ equals H and x3 has an average value of about 9,000 (PEG 9-M is also known as Polyox WSR® N-3333 available from Union Carbide); and PEG-14 M wherein $R^{201}$ equals H and x3 has an average value of about 14,000 (PEG-14M is also known as Polyox WSR® N-3000 available from Union Carbide).

Other Additional Comronents

The compositions of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate, antidandruff agents such as zinc pyridinethione; and optical brighteners, for example polystyryistilbenes, triazinstilbenes, hydroxycoumarins, aminocoumarins, triazoles, pyrazolines, oxazoles, pyrenes, porphyrins, imidazoles, and mixtures thereof.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

The compositions of the present invention are suitable for rinse-off products and leave-on products, and are particularly useful for making products in the form of emulsion, cream, gel, spray or, mousse.

Examples 1 through 6 are hair conditioning compositions of the present invention which are particularly useful for rinse-off use.

| | Compositions | | | | | |
|---|---|---|---|---|---|---|
| Components | Ex. 1 | Ex. 2 | Ex. 3 | Ex. 4 | Ex. 5 | Ex. 6 |
| Pentaerythritol Tetra-isostearate *1 | 1.0 | — | 0.5 | — | — | — |
| Pentaerythritol Tetraoleate *2 | — | 1.0 | — | 0.5 | — | — |
| Trimethylolpropane Trioleate *3 | — | — | 0.5 | 0.5 | 1.0 | 1.0 |
| Trimethylolpropane Triisostearate *4 | — | — | — | — | — | 1.0 |
| Dihydrogenated Tallow-amidoethyl Hydroxy-ethylmonium Methosulfate *5 | 1.0 | 2.0 | — | — | — | 1.5 |
| Distearamidoethyl hydroxy-ethylmonium methosulfate | — | — | 1.0 | 2.0 | 1.0 | — |
| Cetyl Alcohol *6 | 4.5 | 4.5 | 4.0 | 4.0 | 4.5 | 4.5 |
| Stearyl Alcohol *7 | 2.5 | 2.5 | 2.0 | 2.5 | 2.5 | 2.5 |
| Behenyl Alcohol *8 | — | 1.0 | — | 1.0 | 0.5 | — |
| Stearamidopropyl Dimethylamine *9 | 2.0 | 2.0 | 2.0 | 2.0 | 2.0 | 2.0 |
| l-Glutamic Acid *10 | 0.64 | 0.64 | 0.8 | 0.6 | 0.64 | 1.8 |
| Hydroxyethyl Cellulose *11 | — | — | — | — | 0.5 | 0.1 |
| Polyoxyethylene (2000) *12 | 0.1 | — | 0.1 | — | — | — |
| Polyquaternium-10 *13 | — | — | — | — | 0.05 | 0.05 |
| Polyquaternium-7 *14 | — | — | — | 0.05 | — | — |
| Preservatives | 0.04 | 0.04 | 0.04 | 0.04 | 0.04 | 0.04 |
| Benzyl alcohol | 0.4 | 0.4 | 0.4 | 0.4 | 0.4 | 0.4 |
| Perfume | 0.25 | 0.25 | 0.25 | 0.25 | 0.25 | 0.25 |
| Silicone Blend *15 | 2.0 | 2.5 | 4.2 | 2.5 | 2.5 | 2.5 |
| Silicone Emulsion *16 | — | — | — | 0.5 | 0.5 | 0.5 |
| Hydrolyzed collagen *17 | 0.01 | 0.01 | 0.01 | 0.01 | 0.01 | 0.01 |
| Vitamin E *18 | 0.01 | 0.01 | 0.01 | 0.01 | 0.01 | 0.01 |
| Panthenol *19 | 0.03 | 0.03 | 0.03 | 0.03 | 0.03 | 0.03 |
| Panthenyl Ethyl Ether *20 | 0.25 | 0.25 | 0.25 | 0.25 | 0.25 | 0.25 |
| Citric Acid *21 | amount necessary to adjust pH 3–7 | | | | | |
| Deionized Water | q.s. to 100% | | | | | |

Definitions of Components
*1 Pentaerythritol Tetraisostearate: KAK PTI obtained by Kokyu alcohol.
*2 Pentaerythritol Tetraoleate: Available from Shin-Nihon Rika.
*3 Trimethylolpropane Trioleate: Enujerubu TP3SO obtained by Shin-Nihon Rika.
*4 Trimethylolpropane Triisostearate: KAK TTI obtained by Kokyu alcohol.
*5 Dihydrogenated Tallowamidoethyl Hydroxyethylmonium Methosulfate: Varisoft 110 obtained by Witco.

-continued

| Compositions | | | | | | |
|---|---|---|---|---|---|---|
| Components | Ex. 1 | Ex. 2 | Ex. 3 | Ex. 4 | Ex. 5 | Ex. 6 |

*6 Cetyl Alcohol: Konol series obtained by Shin-Nihon Rika.
*7 Stearyl Alcohol: Konol series obtained by Shin-Nihon Rika.
*8 Behenyl Alcohol: 1-Docosanol (97%) obtained by Wako.
*9 Stearamidopropyl Dimethylamine: Amidoamine MPS obtained by Nikko.
*10 l-Glutamic Acid: l-Glutamic acid (cosmetic grade) obtained by Ajinomoto.
*11 Hydoxyethyl Cellulose: Available from Aqualon.
*12 Polyoxyethylene (2000): WSR N-10 obtained Amerchol.
*13 Polyquaternium-10: UCARE Polymer LR 400 obtained by Amerchol.
*14 Polyquaternium-7: Merquat S obtained by Calgon.
*15 Silicone Blend: SE76 obtained by GE
*16 Silicone Emulsion: X65-4829 obtained by Tosil/GE.
*17 Hydrolyzed Collagen: Peptein 2000 obtained by Hormel.
*18 Vitamin E: Emix-d obtained by Eisai.
*19 Panthenol: Available from Roche.
*20 Panthenyl Ethyl Ether: Available from Roche.
*21 Citric Acid: Anhydrous Citric acid obtained by Haarman & Reimer.

Method of PreDaration

The compositions of Examples 1 through 6 as shown above can be prepared by any conventional method well known in the art. They are suitably made as follows: If included in the composition, polymeric materials such as hydroxyethyl cellulose, polyoxyethylene, Polyquaternium-10, and Polyquaternium-7 are dispersed in water at room temperature to make a polymer solution. High melting point compounds, hydrophilically substituted cationic surfactant, tertiary amido amines, and the polymer solution, if present, are mixed and heated up to above 70° C. The mixture thus obtained is cooled down to below 50° C., and the remaining components are added with agitation, and further cooled down to about 30° C.

Alternatively, high melting point compounds, tertiary amido amines, and the polymer solution, if present, are mixed and heated up to above 70° C. The mixture thus obtained is cooled down to about 60° C. where the hydrophilically substituted cationic surfactant is added. The final mixture thus obtained is cooled below 50° C., and the remaining components are added with agitation, and further cooled down to about 30° C.

A triblender and/or mill can be used in each step, if necessary to disperse the materials.

The embodiments disclosed and represented by the previous examples have many advantages. For example, they can provide long lasting moisturized feel, smooth feel, and manageability control to the hair when the hair is dried, yet not leave the hair feeling greasy.

It is understood that the examples and embodiments described herein are for illustrative purposes only and that various modifications or changes in light thereof will be suggested to one skilled in the art without departing from its spirit and scope.

What is claimed is:

1. A hair conditioning composition comprising:

(1) a high molecular weight ester oil being water-insoluble, having a molecular weight of at least about 800, and in liquid form at 25° C., the high molecular weight ester oil selected from the group consisting of:

a) pentaerythritol ester oils of the following formula:

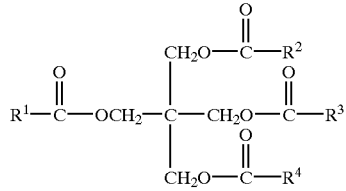

wherein $R^1$, $R^2$, $R^3$, and $R^4$, independently, are branched or straight, saturated or unsaturated alky, aryl, or alkylaryl groups having from 1 to about 30 carbons;

b) trimethylol ester oils of the following formula:

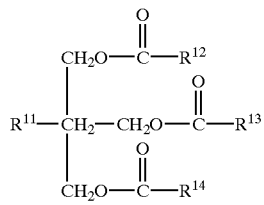

wherein $R^{11}$ is an alkyl group having from 1 to about 30 carbons, and $R^{12}$, $R^{13}$, and $R^{14}$, independently, are branched or straight, saturated or unsaturated alkyl, aryl, or alkylaryl groups having from 1 to about 30 carbons; and mixtures thereof;

(2) a hydrophilically substituted cationic surfactant;

(3) a high melting point compound having a melting point of at least 25° C.; and (4) an aqueous carrier.

2. The hair conditioning composition according to claim 1 wherein the high molecular weight ester oil is selected from the group consisting of pentaerythritol ester oils wherein $R^1$, $R^2$, $R^3$, and $R^4$, independently, are branched or straight, saturated or unsaturated alkyl groups having from about 8 to about 22 carbons, trimeehylol ester oils wherein $R^{11}$ is ethyl and $R^{12}$, $R^{13}$, and $R^{14}$, independently, are branched or straight, saturated or unsaturated alkyl groups having from 8 to about 22 carbons; and mixtures thereof.

3. The hair conditioning composition according to claim 1 wherein the hydrophilically substituted cationic surfactant is selected from the group consisting of dialkylamido ethyl hydroxyethylmonium salt, dialkylamido ethyl dimonium salt, dialkoyl ethyl hydroxyethylmonium salt, dialkoyl ethyldimonium salt, and mixtures thereof.

4. The hair conditioning composition according to claim 1 wherein the high melting point compound is selected from the group consisting of cetyl alcohol, stearyl alcohol, behenyl alcohol, and mixtures thereof.

5. The hair conditioning composition according to claim 4 wherein the high melting point compound is comprised at a level of more than about 4% by weight of the composition.

6. The hair conditioning composition according to claim 1 further comprising a tertiary amido amine having an alkyl group of from about 12 to about 22 carbons.

7. The hair conditioning composition according to claim 6 further comprising an acid selected from the group consisting of l-glutamic acid, lactic acid, hydrochloric acid, malic acid, succinic acid, acetic acid, fumaric acid, l-glutamic acid hydrochloride, tartaric acid, citric acid, and mixtures thereof; wherein the molar ratio of the tertiary amido amine to the acid is from about 1:0.3 to about 1:2.

8. The hair conditioning composition according to claim 1 further comprising a silicone compound.

9. The hair conditioning composition according to claim 1 comprising:

(1) from about 0.1% to about 20% of the high molecular weight ester oil;

(2) from about 0.1% to about 20% of the hydrophilically substituted cationic surfactant;

(3) from about 4% to about 8% of the high melting point compound; and (4) water.

* * * * *

UNITED STATES PATENT AND TRADEMARK OFFICE
CERTIFICATE OF CORRECTION

PATENT NO. : 6,468,515 B1
DATED : October 22, 2002
INVENTOR(S) : Uchiyama et al.

It is certified that error appears in the above-identified patent and that said Letters Patent is hereby corrected as shown below:

Column 1,
Line 28, "stabc" should read -- static --.

Column 3,
Line 63, delete "Oo".

Column 4,
Line 19, "$R^1$" should read -- $R^{11}$ --.

Column 7,
Line 57, "ethyleneg lycol monostea rate," should read -- ethyleneglycol monostearate, --.

Column 8,
Line 12, "NMAseries" should read -- NAA series --.
Line 17, "witco" should read -- Witco --.
Line 60, "andlor" should read -- and/or --.

Column 9,
Line 10, "palmitamidopropyidimethylamine" should read -- palmitamidopropyldimethylamine --.
Line 12, "palmitamidoethyidiethylamine" should read -- palmitamidoethyldiethylamine --.

Column 12,
Line 16, "abovedisclosed" should read -- above disclosed --.

Column 14,
Lines 17 and 18, "quatemium" should read -- quaternium --.

Column 15,
Lines 15, 46 and 52, "quatemary" should read -- quaternary --.
Line 42, "quatemized" should read -- quaternized --.

Column 16,
Line 13, "dimethyidiallylammonium" should read -- dimethyldiallylammonium --.
Line 16, "Polyquatemium" should read -- Polyquaternium --.
Line 55, delete "10".

UNITED STATES PATENT AND TRADEMARK OFFICE
CERTIFICATE OF CORRECTION

PATENT NO. : 6,468,515 B1
DATED : October 22, 2002
INVENTOR(S) : Uchiyama et al.

It is certified that error appears in the above-identified patent and that said Letters Patent is hereby corrected as shown below:

Column 17,
Line 4, "Polyquatemium" should read -- Polyquaternium --.
Line 50, delete "ethyl linolenic acid". (repeated on following line).
Lines 62 and 63, "octyidodecyl" should read -- octyldodecyl --.

Column 18,
Lines 40-41, "tricaprylateltricaprate" should read -- tricaprylate/tricaprate --.

Column 19,
Line 40, "Comronents" should read -- Components --.

Column 20,
Line 5, "polystyryistilbenes" should read -- polystyrylstilbenes --.
Line 62, "Shin-Nihon Rika" should read -- Shin-NihonRika --.
Lines 63-64, "Shin-Nihon Rika" should read -- Shin-NihonRika --.

Column 21,
Line 13, "Hydoxyethyl" should read -- Hydroxyethyl --.
Line 22, "PreDaration" should read -- Preparation --.

Signed and Sealed this

Eighteenth Day of February, 2003

JAMES E. ROGAN
*Director of the United States Patent and Trademark Office*